(12) United States Patent
Shimada et al.

(10) Patent No.: US 10,359,421 B2
(45) Date of Patent: Jul. 23, 2019

(54) INSPECTION KIT (71) Applicants: FUJIFILM Corporation, Tokyo (JP); MIZUHO MEDI CO., LTD., Saga (JP)

(72) Inventors: Kaori Shimada, Saga (JP); Kenji Narahara, Saga (JP)

(73) Assignee: FUJIFILM CORPORATION, Tokyo (JP)

( * ) Notice: Subject to any disclaimer, the term of this patent is extended or adjusted under 35 U.S.C. 154(b) by 43 days.

(21) Appl. No.: 15/520,297

(22) PCT Filed: Oct. 7, 2015

(86) PCT No.: PCT/JP2015/078508
§ 371 (c)(1),
(2) Date: Apr. 19, 2017

(87) PCT Pub. No.: WO2016/084491
PCT Pub. Date: Jun. 2, 2016

(65) Prior Publication Data
US 2017/0315116 A1    Nov. 2, 2017

(30) Foreign Application Priority Data
Nov. 25, 2014   (JP) ................................ 2014-237902

(51) Int. Cl.
*G01N 21/75*   (2006.01)
*G01N 33/543*   (2006.01)
(Continued)

(52) U.S. Cl.
CPC ..... *G01N 33/54386* (2013.01); *G01N 33/543* (2013.01); *G01N 33/558* (2013.01);
(Continued)

(58) Field of Classification Search
CPC .......... G01N 33/54386; G01N 33/558; G01N 33/56983; G01N 33/543; G01N 2469/10; G01N 2333/11
See application file for complete search history.

(56) References Cited

U.S. PATENT DOCUMENTS

| | | | |
|---|---|---|---|
| 5,602,040 | A | 2/1997 | May et al. |
| 6,187,598 | B1 | 2/2001 | May et al. |

(Continued)

FOREIGN PATENT DOCUMENTS

| | | |
|---|---|---|
| EP | 2 330 421 | 6/2011 |
| EP | 2 910 946 | 8/2015 |

(Continued)

OTHER PUBLICATIONS

International Search Report dated Dec. 22, 2015 in corresponding International Application No. PCT/JP2015/078508.

*Primary Examiner* — Dennis White
(74) *Attorney, Agent, or Firm* — Wenderoth, Lind & Ponack, L.L.P.

(57) ABSTRACT

Provided is an inspection kit that proper inspection can be performed even if a tester drips a remainder of sample. The inspection kit includes: a reagent device having a sample-dripping part, the reagent device being capable of making a sample dripped on the sample-dripping part flow in a first direction from an upstream side toward a downstream side; and a case surrounding the reagent device. A liquid-absorbing part is provided with a portion near the sample-dripping part of the case, the liquid-absorbing part guiding, according to capillary action, the remainder of the sample in a second direction differing from the first direction.

6 Claims, 7 Drawing Sheets (51) Int. Cl.
*G01N 33/569* (2006.01)
*G01N 33/558* (2006.01)

(52) U.S. Cl.
CPC ... *G01N 33/56983* (2013.01); *G01N 2333/11* (2013.01); *G01N 2469/10* (2013.01)

(56) References Cited

U.S. PATENT DOCUMENTS

| | | | |
|---|---|---|---|
| 6,228,660 | B1 | 5/2001 | May et al. |
| 6,818,455 | B2 | 11/2004 | May et al. |
| 7,109,042 | B2 | 9/2006 | May et al. |
| 7,674,615 | B2 | 3/2010 | Ramel et al. |
| 8,802,426 | B2 | 8/2014 | Mori et al. |
| 8,999,730 | B2 | 4/2015 | Oyamada et al. |
| 2001/0008774 | A1 | 7/2001 | May et al. |
| 2001/0041368 | A1 | 11/2001 | May et al. |
| 2005/0244986 | A1 | 11/2005 | May et al. |
| 2006/0008847 | A1 | 1/2006 | Ramel et al. |
| 2009/0181470 | A1 | 7/2009 | Chiku et al. |
| 2010/0226822 | A1 | 9/2010 | Ramel et al. |
| 2011/0136142 | A1 | 6/2011 | Oyamada et al. |
| 2011/0269247 | A1 | 11/2011 | Chiku et al. |
| 2012/0058465 | A1* | 3/2012 | Mori ............... G01N 33/54386 435/5 |
| 2014/0295405 | A1 | 10/2014 | Wada et al. |

FOREIGN PATENT DOCUMENTS

| | | |
|---|---|---|
| JP | 9-178748 | 7/1997 |
| JP | 2002-202307 | 7/2002 |
| JP | 2007-536521 | 12/2007 |
| JP | 2009-216695 | 9/2009 |
| JP | 2010-230634 | 10/2010 |
| JP | 2011-99734 | 5/2011 |
| JP | 2011-117906 | 6/2011 |
| JP | 2012-168051 | 9/2012 |
| JP | 2014-209097 | 11/2014 |
| WO | 2005/108991 | 11/2005 |
| WO | 2014/114949 | 7/2014 |

* cited by examiner

INSPECTION KIT

BACKGROUND OF THE INVENTION

1. Field of the Invention

The present invention relates to an inspection kit including a reagent device in accordance with the immunochromatography method.

2. Description of the Related Art

In recent years, inspection kits by means of the immunochromatography method have been often used for inspection with respect to infectious disease which especially requires quick diagnosis.

The wider use of such kits has enabled to quickly and easily specify pathogenic infection to patients, thereby rapidly performing subsequent diagnosis and medical treatment suitably.

Infectious disease-causing pathogens may be bacteria, viruses, or the like.

Influenza viruses, which represent the infectious disease-causing pathogens, may infect many animals including human beings to cause influenza.

If human beings are infected with influenza viruses, after an incubation period of several days, condition such as fever, headaches, joint pain, weakness, coughs, and sore throats, or the like may be caused thereby.

In many cases, bronchitis, pneumonia, otitis media, or the like may be developed.

Furthermore, encephalopathy, myositis, myocarditis, or the like may be also caused to fall into a critical condition.

In particular, this may be a matter of life and death for elderly people and/or infants lacking physical strength.

As soon as possible after the appearance of the disease, diagnosis should be made.

Upon a positive reaction, the patient should be isolated to prevent from infection expansion, and medical treatment by means of suitable medicine should be performed on him/her. This is very effective.

As recited in Reference 1 (Japanese patent application Laid-open No. H09-178748), the immunochromatography method has been originally developed for such as a pregnancy test by herself or the like.

The method, however, has a wide applicable range, does not require specific equipment/apparatuses, and operation thereof is very simple. This is remarkably useful, since a measurement result can be obtained by: adding a sample which may contain an analysis object onto a test according thereto; and settling the test for a short time.

For this reason, the method has been widely adopted as an easy and rapid measurement method with high specificity for diagnosis of infectious disease not only in general hospitals with comparatively large scales but also in family doctors/clinics easily visited by patients.

The patients can be diagnosed at the nearest medical institution, which may greatly help speedup of medical practice, and preventing the patients from concentrating at a specific medical institution.

Reagent devices in accordance with the immunochromatography method utilize antigen/antibody reaction, and it is sufficient to merely drip a liquid sample to be detected which may contain an analysis object (an antigen) thereto.

If so, in the inside of a membrane (i.e. nitrocellulose membrane), colored particle-labeled antibody provided with a colored particle-labeled antibody application part in a dried condition is eluted and removed according to capillary action there-through.

Other active components (antibodies) have been fixed in a shape of line in the middle of the membrane. The colored particle-labeled antibody is captured by one of the other active components like a sandwich to form coloration in the shape of the line, thereby visualizing a measurement result.

A reagent device includes: a sample-dripping part on which a sample that may contain an analysis object is dripped; a colored particle-labeled antibody application part; a detection line part on which antibodies have been bonded in a shape of line with a membrane; a water suction part; and so on.

Furthermore in general, a control line part for confirming whether or not the sample has normally flowed so as to react is also provided with a downstream side of the detection line part on the membrane.

In many cases, the reagent device is enclosed in a plastic case to be supplied as an inspection kit in order to improve the operability of the reagent device and to reduce risks of infection and/or contamination.

A sensitization method has been also devised. The method includes: further applying the principle of this immunochromatography method; making gold colloid (labeled particles) react with silver ions in the presence of reducing agents; and drastically increasing color intensity according to deposition of the silver, thereby sensitizing the sensitivity.

Reference 2 (Japanese patent application Laid-open No. 2010-230634), Reference 3 (Japanese patent application Laid-open No. 2011-99734, and Reference 4 (Japanese patent application Laid-open No. 2011-117906) recite silver-sensitizer techniques. Inspection kits usable for influenza viruses by means of the silver-sensitizer techniques including not only reagent devices but also sensitization liquid have been commercially available.

Upon installing one of the inspection kits in an exclusive measurement apparatus, the measurement apparatus automatically performs measurement as well as determination with respect to the installed kit.

For this reason, it is sufficient for a tester to merely perform the followings steps of: extracting a sample from patient's nasal cavity and/or patient's pharynx by means of a sterilized cotton swab; inserting the swab into exclusive extraction liquid; dripping a predetermined amount of the liquid onto the sample-dripping part of the inspection kit; and attaching the kit into the measurement apparatus.

After the attachment, the measurement apparatus automatically performs all necessary processes. A determination result obtained by having measured color development on the line can be also printed out.

Ten times or more sensitivity larger than the sensitivity of the general immunochromatography method can be obtained, and the determination result thereby also has higher objectivity.

Meanwhile, only a small amount of the viruses exist on an affected part of a patient shortly after the onset of symptoms. If the sensitivity of the inspection kits is not high, detection of the viruses tends to be impossible resulting in negative result at that time.

In other words, the high sensitivity system utilizing the sensitization is very effective for more early finding out infection patients to suitably isolate and/or medically treat them, thereby preventing from expanding the infection disease.

Regarding the immunochromatography method without utilizing the sensitization, inspection kits used for various kinds of infectious disease have been put in practical use. The various kinds of viruses include other than the influenza viruses: adenoviruses; hemolytic streptococus; noroviruses; or the like.

In these cases, a small amount of sample is extracted, for example, by: wiping patient's pharynx and/or nasal cavity (the affected part) by means of a cotton swab; or sampling excrement specimen. And then, the extracted sample is immersed into extracting solution filled up with a small vessel so as to elute reaction components (antigens) of viruses and/or bacteria therein.

After that, an eyedropper nozzle is attached with an opening of the vessel, and a necessary amount of the eluted solution should be dripped onto the sample-dripping part of the inspection kit, while pushing the vessel from the outside thereof.

In general, it is preferable that an amount of about three or four drips is dripped thereon.

However, in a very busy environment such as an influenza epidemic term, testers drip samples in a hurry, are often under the impression that droplets are insufficient. So, the testers tend to put a remainder of sample into the inspection kits, and/or drip the same repeatedly by mistake.

As a result, the amount of dripped sample may result in two or three times of the preferable amount in many cases.

In these cases, the remainder of sample overflows the (upper) surface(s) of the colored particle-labeled antibody application part and/or the membrane without gently flowing according to the capillary action.

This causes a phenomenon that colored particle-labeled antibodies neither cannot be dissolved or flow so as to stay on the application part. In other words, the antibodies are left behind the overflowing sample.

Also in the detection part, neither the colored particle-labeled antibodies nor the sample effectively pass through the (inner) detection line part bonded with reaction components (antibodies) of the membrane. The sample further overflows the (upper) surface(s) thereof.

There is no chance which three elements necessary for immunoreation of: the antibodies bonded with the membrane; antigens contained in the sample; and the colored particle-labeled antibodies contact with each other. Accordingly, neither first color development at the detection line part nor second color development at the control line part is generated.

Even if the sample is positive, this results in the followings: sufficient sensitivity cannot be obtained at the detection line part; and enough color development cannot be also obtained at the control line.

As discussed above, in a case where the amount of dripped sample is surplus, there may be problems including: re-inspection is needed without sufficient color development at the control line; and false negative result may be made without enough detection sensitivity.

In the system using sensitization liquid recited in Reference 2 through Reference 4, the situation becomes still more serious.

In addition to the problem of the general reduced sensitivity in the immunochromatography method, there is a further problem. That is, each of washing deployment and immersion of the sensitization liquid is inhibited so that sensitizing reaction does not proceed well.

In the sensitization system, the affectivity of inspection is judged when a measurement apparatus performs automatically reading. Accordingly, if the color intensity at the control line does not increase due to the sensitization, the inspection itself may be regarded as an error, thereby obtaining no inspection result.

Even if such a situation occurs, in many cases, the testers cannot understand that the situation has been caused by the operation of them. Then, the testers tend to wonder the reliability of the inspection. This result is highly discouraged.

In short, since prior art fails to provide countermeasures against a case where the testers drip the remainder of sample, there are following problems. That is, the inspection itself cannot be established, and the inspection result may be incorrect caused by generating false negative result and/or false positive result.

LIST OF CITED REFERENCES

Reference 1: Japanese patent application Laid-open No. H09-178748;
Reference 2: Japanese patent application Laid-open No. 2010-230634;
Reference 3: Japanese patent application Laid-open No. 2011-99734; and
Reference 4: Japanese patent application Laid-open No. 2011-117906.

OBJECTS AND SUMMARY OF THE INVENTION

In view of the above, an object of the present invention is to provide an inspection kit that proper inspection can be performed even if a tester drips a remainder of sample.

A first aspect of the present invention provides an inspection kit, comprising: a reagent device having a sample-dripping part, the reagent device being capable of making a sample dripped on the sample-dripping part flow in a first direction from an upstream side toward a downstream side; and a case surrounding the reagent device, wherein a liquid-absorbing part is provided with a portion near the sample-dripping part of the case, the liquid-absorbing part guiding, according to capillary action, a remainder of the sample in a second direction differing from the first direction.

If the tester drips a remainder of sample, this structure enables to guide the remainder of the sample in the second direction different from the first direction according to the capillary action. As a result, only a suitable amount of sample flows through the reagent device to easily obtain a correct inspection result.

Meanwhile, when the tester drips a suitable amount of sample onto the sample-dripping part, the liquid-absorbing part does not guide the sample. As a result, the sample flows through the reagent device in the first direction to obtain another correct inspection result.

A second aspect of the present invention provides, in addition to the first aspect, wherein the second direction intersects the first direction.

A third aspect of the present invention provides, in addition to the second aspect, wherein the second direction orthogonally intersects the first direction.

A fourth aspect of the present invention provides, in addition to the first aspect, wherein the first direction and the second direction are opposite to each other.

With these structures, the second direction is variously set up. In any case, if the tester drips a remainder of sample onto the sample-dripping part, only a suitable amount of sample flows through the reagent device to easily obtain a correct inspection result.

A fifth aspect of the present invention provides, in addition to the first aspect, wherein the case includes: an upper case surrounding an upper part of the reagent device; and a lower case surrounding a lower part of the reagent device.

In a case where sensitization liquid is not used, if the tester drips a remainder of sample, only a suitable amount of sample flows through the reagent device to easily obtain a correct inspection result.

A sixth aspect of the present invention provides, in addition to the fifth aspect, wherein: the case further includes an intermediate plate located between the upper case and the lower case; and the intermediate plate includes: a first sensitizer pot storing first sensitizer containing a reducing agent therein; and a second sensitizer pot storing second sensitizer containing silver ion liquid therein.

In another case where the sensitization liquid is used, if the tester drips a remainder of sample, only a suitable amount of sample flows through the reagent device to easily obtain a correct inspection result. In addition to the above, simultaneously both of washing deployment and immersion of the sensitization liquid is normally performed so that sensitizing reaction well proceeds.

Effect of Invention

As discussed above, not only in a case where the sensitization liquid is used but also in another case where the sensitization liquid is not used, according to the present invention, only a suitable amount of sample flows through the reagent device to easily obtain a correct inspection result.

Meanwhile, when a dripped amount is suitable, and the liquid-absorbing part affects neither the flow nor the reaction, thereby enabling to originally perform precise inspection.

BRIEF DESCRIPTION OF THE DRAWINGS

FIG. 11 (*a*) is a perspective view of a lower case and a reagent device in Embodiment 2 (Example 1) according to the present invention;

FIG. 11 (*b*) is a perspective view of a lower case and a reagent device in Embodiment 2 (Example 2) according to the present invention;

FIG. 12 (*a*) is a perspective view of a lower case and a reagent device in Embodiment 2 (Example 3) according to the present invention; and FIG. 12 (*b*) is a perspective view of a lower case and a reagent device in Embodiment 2 (Example 4) according to the present invention.

BRIEF DESCRIPTION OF SYMBOLS

1: Adhesive sheet
2: Sample-dripping part
3: Colored particle-labeled antibody application part
4: Solid phased-antibody membrane
4*a*: Detection line part
4*b*: Control line part
5: Water suction paper
10: Reagent device
11: Inspection kit
110: Upper case
111: First liquid-absorbing part
112: Sample-dripping part
120: Lower case
121: Second liquid-absorbing part
122: Reagent device-installing part
123: Detection window
124: Pin
130: Intermediate plate
131: Cleaning fluid-added pad
132: Cleaning fluid-absorbing pad
133: First sensitizer pot
134: Second sensitizer pot
135: Engaging hole

DETAILED DESCRIPTION OF THE PREFERRED EMBODIMENTS (Outline of Invention)

Hereinafter, prior to concretely explaining Embodiments of the present invention, the outline of the present invention will now be described.

In the present invention, a sample-dripping part is arranged near a liquid-absorbing part in the inside of an inspection kit for the immunochromatography method. The liquid-absorbing part absorbs sample liquid according to the capillary action.

The liquid-absorbing part may be composed of slits, for example, and play a role of: guiding, when a remainder of sample has been dripped, overflowing liquid to the periphery of a reagent device; and holding the overflowing liquid therein.

It is sufficient for the liquid-absorbing part to be capable of absorbing the remainder of the sample according to the capillary action. Various structures, such as hydrophilic porous bodies, meshwork structures, brush structures, and parallel arrangement of a plurality of columns and/or plates can be conceived to be used for the liquid-absorbing part.

The liquid-absorbing part may absorb the liquid overflowing from the remainder of dripped sample liquid due to the capillary action.

In this way, guiding the remainder of dripped sample to the liquid-absorbing part causes for a proper amount of the sample to flow through the reagent device to a downflow side. Thereby, neither colored particle-labeled antibodies stay as they are, nor the sample overflows the (upper) surface(s) thereof. So, the above-mentioned problems can be avoided.

As a result, the inspection result can be established, and the false negative result and/or the false positive result can be avoided.

The sample capable of being supplied for the chromatographic method of the present invention may contain an analysis object. In this context, there is no specific limitation. The sample is solution that a suitable solvent contains a biological sample. The biological sample may be body liquid of humans and/or animals (for example, blood, serum, plasma, cerebrospinal fluid) and/or a sample extracted from a portion and/or a part of the body by wiping and/or abrasion (for example, pharynx-wiping liquid, nasal cavity-wiping liquid) and/or feces/secretions (nasal discharge, sputum, feces, lacrimal fluid, sweat, urine), or the like.

The solution may normally include buffer solution containing a surface active agent or the like so as to extract the analysis object.

Embodiments of the present invention are now described with reference to the accompanying drawings.

Embodiment 1

<Outline>

Figure 1:
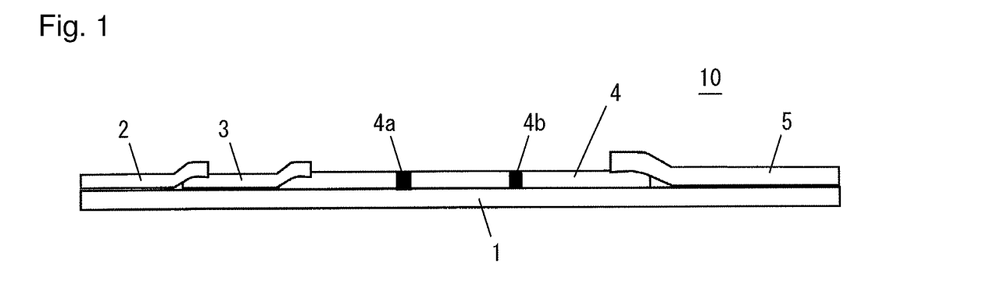
FIG. 1 is a side view of a reagent device in Embodiment 1 according to the present invention.
Figure 2:
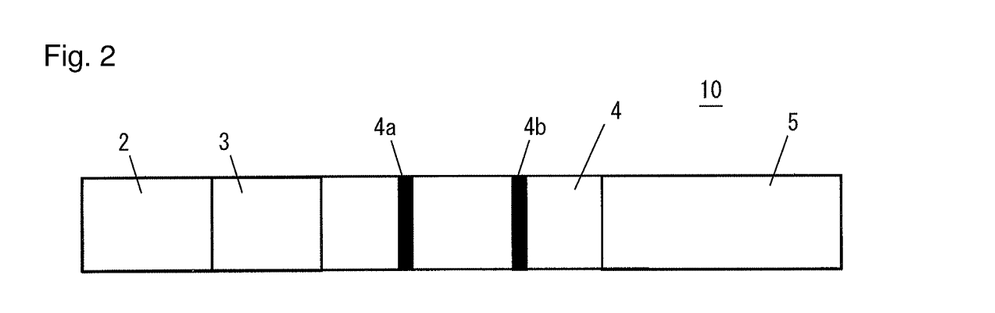
FIG. 2 is a plan view of the reagent device in Embodiment 1 according to the present invention.
Figure 3:
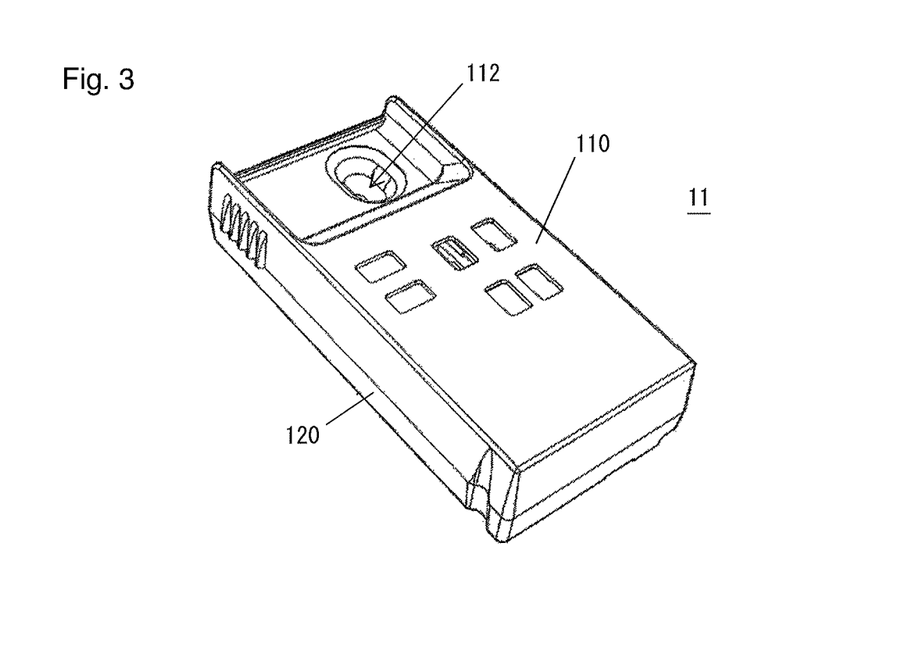
FIG. 3 is a perspective view of an inspection kit in Embodiment 1 according to the present invention.

FIG. 1 is a side view of a reagent device in Embodiment 1 according to the present invention, FIG. 2 is a plan view of the reagent device in Embodiment 1 according to the present invention, and FIG. 3 is a perspective view of an inspection kit in Embodiment 1 according to the present invention.

In Embodiment 1, an inspection kit 11 includes cases 110 and 120 made of plastic. A reagent device 10 is located in the inside of the cases 110 and 120. Furthermore, a detection window 123 and/or a window made of transparent plastic through which a detection part of the reagent device 10 can be seen from the outside are/is formed on the cases 110 and 120.

The reagent device 10 includes a sample-dripping part 2 of an upstream side, and a suction paper 5 of a downstream side that is the opposite side of the upstream side. The reagent device 10 makes a sample flow there-through according to the capillary action in a first direction from the upstream side to the downstream side.

Especially in Embodiment 1, the inspection kit 11 includes reducing agents for silver compounds and silver ions therein to improve sensitivity due to sensitization reaction as the core of a complex of: an analysis object conjugated with a fixed reagent; and a labeled molecule.

More concretely as described in detail later, the inspection kit 11 is provided with an intermediate plate 130 including therein: a cleaning fluid-added pad 131; a cleaning fluid-absorbing pad 132; a first sensitizer pot 133; and a second sensitizer pot 134, which are required for the sensitization reaction.

In position close to the sample-dripping part 2 of the reagent device 10 surrounded by the cases 110 and 120, liquid-absorbing parts 111 and 121 is provided to be capable of guiding and holding, according to the capillary action, liquid overflowing when a remainder of sample has been dripped.

According to Embodiment 1, even if the remainder of sample has been dripped, the liquid-absorbing parts 111 and 121 provided with the cases 110 and 120 enable to promptly perform the immunochromatography method without false negative result or false positive result.

<Reagent Device>

A reagent device applicable for the chromatographic method in Embodiment 1 can be obtained by a general method as recited in Reference 1.

There is no limitation with respect to the reagent device for the method as long as the reagent device 10 can be used for the general immunochromatography method.

As shown in FIG. 1 and FIG. 2, the reagent device 10 is configured by arranging on an adhesive sheet 1: the sample-dripping part 2; the colored particle-labeled antibody application part 3; a solid phased-antibody membrane 4; and the suction paper 5 in this order in a developing direction from the upstream side to the downstream side.

A solid phased-antibody membrane 4 includes: a detection line part 4a of an area with which antibodies specifically conjugating with an analysis object have been bonded as a detection part; and further a control line part 4b of another area with which other control antibodies have been bonded when desired.

<Labeled Molecule (Colored Particle)>

There is no special limitation with respect to a labeled molecule usable for Embodiment 1.

A colored particle that can been seen by eyes and/or a labeled molecule that enable to be detected due to reaction, for example, a metal micro particle (metallic colloid), a colored latex particle, or the like can be used.

From the point of view of the catalyst activity, a metal micro particle is preferable upon sensitizing signals according to metal deposition to a labeled molecule caused by reduction reaction of metal ions while using the labeled molecule as catalyst.

<Specific Ligand for Labeling>

In the immunochromatography method in Embodiment 1, the labeled molecule is conjugated with specific ligand with affinity to the analysis object, and then is used.

As long as specifically conjugating with the analysis object, there is no limitation with respect to the specific ligand. For example, an antibody versus an antigen, another antigen versus another antibody, a probe versus a gene product, or the like may be conceived.

Preferably, the ligand is an antibody.

In the immunochromatography method in Embodiment 1, there is no specific limitation with respect to the antibody with specificity to the analysis object.

For example, antiserum prepared from animal serum immunized with the antigen of the analysis object, immunoglobulin fraction purified from the antiserum, monoclonal antibodies prepared by fusion between a myeloma cell and an antibody-forming cell derived from a mouse; and at least one fragment of the above (e.g. F(ab') 2, Fab, Fab', or Fv) can be used.

Preparation of the above antibodies may be performed with a usual method.

The labeled molecule and the specific ligand are conjugated/bonded with each other according to a chemical and/or physical method to be used for the reagent device.

This compound (conjugate) is labeled molecule-conjugated specific ligand, which is represented by the colored particle-labeled antibody.

However as mentioned above, both the labeled molecule and the specific ligand may be selected from various options.

Furthermore, two or more kinds of colored particle-labeled antibodies may also be used in a mixed mode.

The above may be diluted with suitable buffer solution or the like, and be applied onto a grass fiber pad and/or a nonwoven fabric to be dried, thereby preparing the colored particle-labeled antibody application part.

<Solid Phased-Antibody Membrane>

It is preferable that a chromatograph carrier used for the solid phased-antibody membrane 4 possesses a structure and a pore size that enable the sample and the labeled molecule to move there-through according to the capillary action, and that material capable of being bonded with capturing ligand specifically reacting with the analysis object is used for the carrier.

In general, a porous membrane carrier is preferable, and a nitrocellulose membrane is especially preferable for the same.

Normally, capturing ligand specifically reacting with the analysis object is made to bond with a part of chromatograph carrier to produce a detection line part 4a.

The detection line part 4a can be produced by physically or chemically bonding the capturing ligand directly to the part of chromatograph carrier.

It is preferable to apply the ligand in a shape of line or dots so as to easily be detected as a signal cased by reaction products.

As long as specifically conjugating with the analysis object, there is no limitation with respect to the capturing ligand. For example, an antibody versus an antigen, another antigen versus another antibody, a probe versus a gene product, or the like may be conceived.

Furthermore in general, the control line part 4b is also provided with a downstream side of the detection line part 4a on the membrane. The control line part 4b is used for confirming whether or not the sample flows to react normally.

The control line part 4b is made to always capture flowing colored particles regardless of presence/absence of an antigen contained in the sample. For example, in a case where the analysis object is a monoclonal antibody of a mouse, anti-mouse IgG polyclonal antibodies are bonded on the membrane, thereby producing the control line part 4b.

<Inspection Kit>

The inspection kit 11 for performing measurement by means of sensitization reaction in Embodiment 1 will now be explained.

Figure 4:
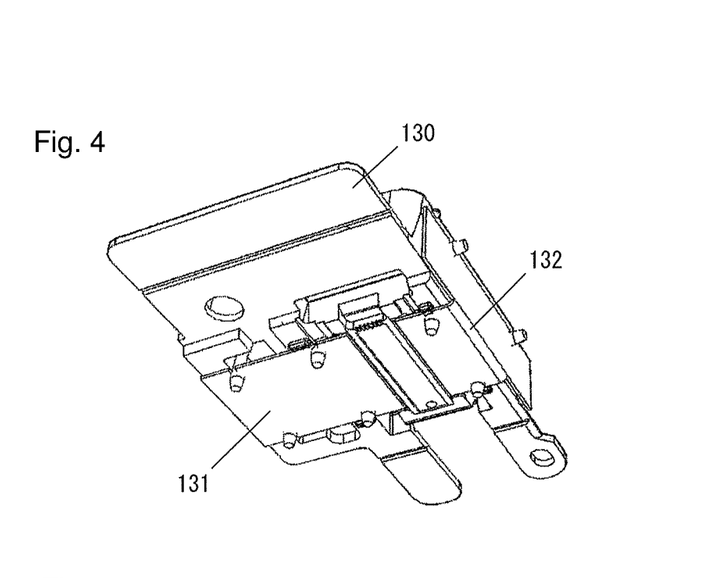
FIG. 4 is a perspective view of an intermediate plate from a bottom side in Embodiment 1 according to the present invention.
Figure 5:
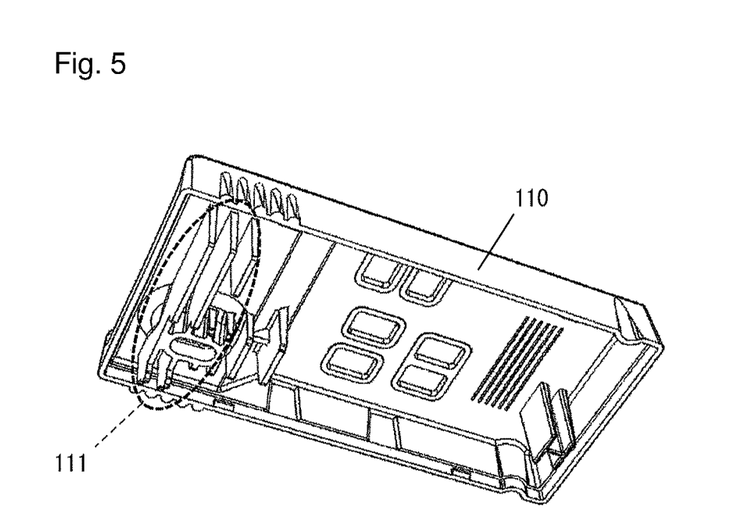
FIG. 5 is a perspective view of an upper case from the bottom side in Embodiment 1 according to the present invention.
Figure 6:
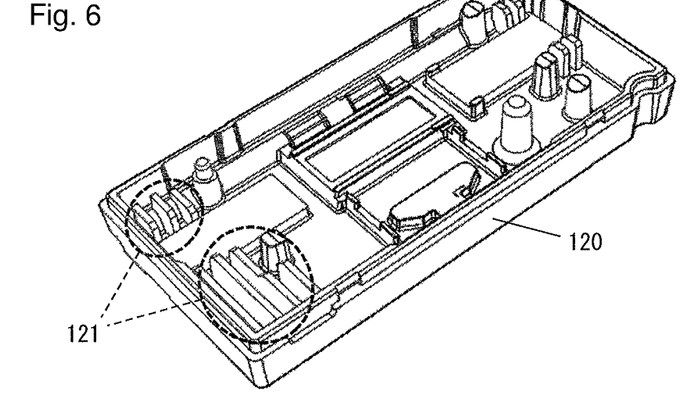
FIG. 6 is a perspective view of a lower case in Embodiment 1 according to the present invention.
Figure 7:
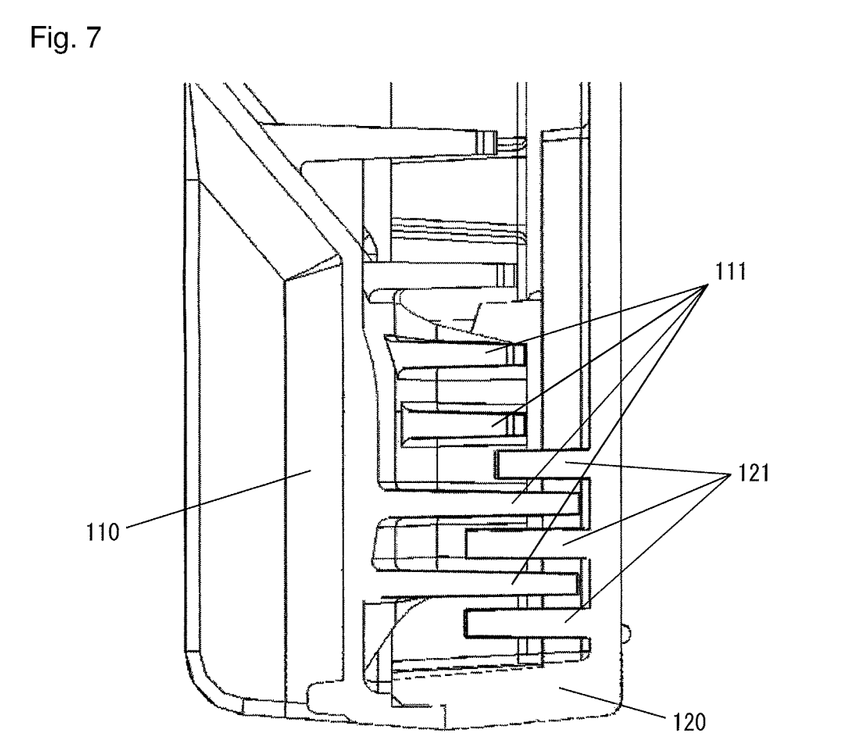
FIG. 7 is a longitudinal section showing a liquid-absorbing part in Embodiment 1 according to the present invention.
Figure 8:
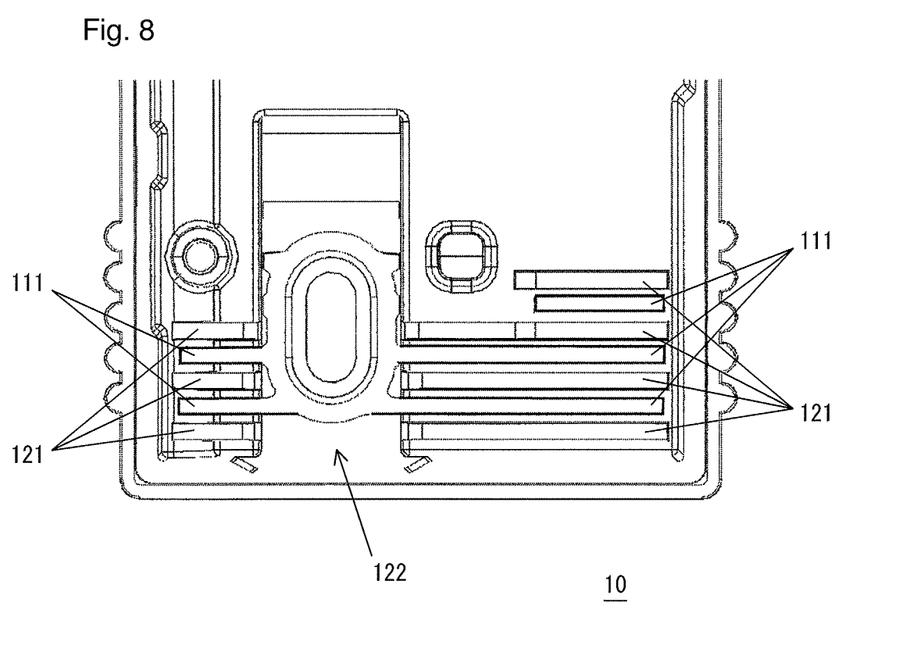
FIG. 8 is a horizontal sectional view showing the liquid-absorbing part in Embodiment 1 according to the present invention.
Figure 9:
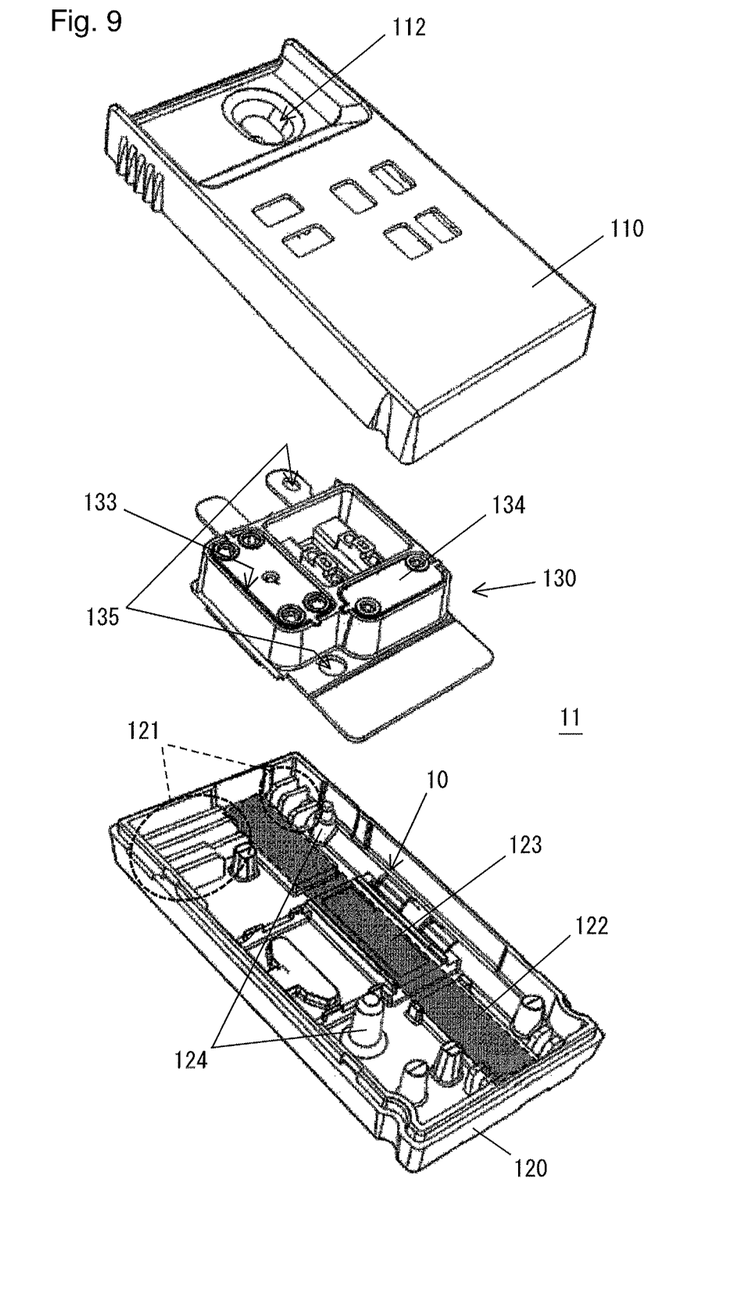
FIG. 9 is an exploded perspective view of the inspection kit in Embodiment 1 according to the present invention.

Herein, FIG. 4 is a perspective view of an intermediate plate from a bottom side in Embodiment 1 according to the present invention, FIG. 5 is a perspective view of an upper case from the bottom side in Embodiment 1 according to the present invention, FIG. 6 is a perspective view of a lower case in Embodiment 1 according to the present invention, FIG. 7 is a longitudinal section showing a liquid-absorbing part in Embodiment 1 according to the present invention, FIG. 8 is a horizontal sectional view showing the liquid-absorbing part in Embodiment 1 according to the present invention, and FIG. 9 is an exploded perspective view of the inspection kit in Embodiment 1 according to the present invention.

As shown in FIG. 9, the inspection kit 11 includes: a case of main three parts (a lower case 120, an intermediate plate 130, and an upper case 110); and the reagent device 10 surrounded by the case.

The reagent device 10 is installed on a reagent device-installing part 122 of the lower case 120. A pin 124 projecting upward from a predetermined portion of a lower case 120 is inserted into an engaging hole 135 opened at a corresponding position of the intermediate plate 130. The intermediate plate 130 is placed on the lower case 120. While keeping the intermediate plate 130 interposed, the upper case 110 is attached with the lower case 120 to surround the reagent device 10 thereby.

As shown in FIG. 5, a first liquid-absorbing part 111 including comb-like first slits projecting downward is provided with the inside of the upper case 110. As shown in FIG. 6, a second liquid-absorbing part 121 including comb-like second slits projecting upward from the inside of the lower case 120 is also provided.

The first slits and the second slits are arranged alternately. Upon having attached the upper case 110 to the lower case 120, as shown in FIG. 7 and FIG. 8, the first slits and the second slits are alternately incorporated to constitute a liquid-absorbing part including the first and second slits.

Herein, it is preferable to design the structure such that spaces of about 0.5 [mm] are formed between the first slits and the second slits, respectively.

As shown in FIG. 4, a bottom side of the intermediate plate 130 is equipped with: a cleaning fluid-added pad 131; and a cleaning fluid-absorbing pad 132.

As shown in FIG. 9, a first sensitizer pot 133 and a second sensitizer pot 134 are provided with an upper portion of the intermediate plate 130, respectively. The first sensitizer pot 133 stores reducing agents, and the second sensitizer pot 134 stores silver ion liquid, respectively.

Since the upper case 110 and the lower case 120 are produced and supplied as a plastic molded article in general, it is preferable to form also the liquid-absorbing part itself as the same article with the same material.

If doing so, as the same raw material, generally used material such as ABS resin, polystyrene, polycarbonate, polypropylene, or the like may be used.

An opening and/or the detection window 123 of transparent material may be formed so as to observe the detection line part 4a of the reagent device 10 from the outside thereof.

As the transparent material, polystyrene and polycarbonate may be preferably used.

When forming the slits at the liquid-absorbing parts 111 and 121 of the upper case 110 and the lower case 120, spaces of preferably 1 [mm] or less, or more preferably 0.5 [mm] or less may be formed.

It is the most preferable that a second direction in which the slits are formed intersects perpendicularly to a first direction in which the sample flows from the sample-dripping part 2.

However, a case where the second direction intersects not perpendicularly to the first direction and another case where the first direction and the second direction are opposite to each other are practically sufficient.

As long as near the sample-dripping part 2, a portion with which the liquid-absorbing part is provided can be optionally selected.

Taking the costs into consideration, it is preferable to integrally mold both the upper case 110 and the lower case 120 with the same plastic.

Furthermore, the upper case 110 and the lower case 120 may not be separated with each other but be partially belt-like connected to each other. If so, they can be folded up to be attached with each other.

It is also theoretically possible to install the slits only on one of the upper case 110 and the lower case 120. The scope of the present invention also includes such a structure.

In practical production, however, upon installing the slits with spaces of 1 [mm] or less on the same molded article, it may become difficult to release the molded article from a mold.

A method is effective, the method including: alternately arranging the first slits of the upper case 110 and the second slits of the lower case 120; and making the alternately arranged slits adjoin with each other to complete the final slits in the assembly thereof.

It is also possible to make distal ends of the slits installed on the upper case 110 approach a bottom surface of the lower case 120 to form slits for holding the remainder of liquid also at this portion.

Furthermore, the first slits of the upper case 110 may be located such that the first slits contact with an upper surface of the reagent device 10 so as to easily guide the remainder of sample to the slits.

This structure causes the surplus amount of sample to go along the upper surface to be easily guided to the peripheral slits.

It is preferable for the slits produced in this way to have enough volume capable of bringing and storing the surplus amount of (liquid) sample therein.

Example 1

<Detection of Influenza Antigen Using Sensitization System>

Referring to Reference 4, the inspection kit for Influenza A viruses has been produced as follows, and measurement using the same has been performed.
<Preparation of Labeling Component>

0.3 [μm] of colored latex and the 0.06 [μm] of gold colloid, which are labeling components, have been used as labeled molecules.

Anti-Influenza A monoclonal antibodies have been used as labeling specific ligand. Conjugation of the above has been performed with a usual method.
<Preparation of Colored Particle-Labeled Antibody Application Part>

Prepared solution containing: anti-Influenza A monoclonal-antibody conjugated colored latex; and an anti-Influenza A monoclonal-antibody conjugated gold colloid with optional concentration, has been applied onto a grass fiber pad to be dried, thereby preparing the colored particle-labeled antibody application part.
<Preparation of Solid Phased-Antibody Membrane>

Anti-Influenza A monoclonal antibodies have been applied onto a predetermined portion of a nitrocellulose membrane (Millipore Corporation: High Flow membrane HF135 (trademark)), which is a porous carrier, in a shape of line at 0.5 [μL] per test, thereby forming the detection line part 4a.

The anti-mouse antibodies have been similarly applied onto the downstream side of the inspection part at 0.5 [μL] per test to form the control line part 4b for checking the reaction.

After the application, air drying is merely necessitated for drying the antibodies to be fixed, thereby preparing the solid phased-antibody membrane for detecting Influenza A viruses.
<Production of Reagent Device>

As shown in FIG. 1, a filter as the sample-dripping part 2, the colored particle-labeled antibody (anti-Influenza A monoclonal antibody) application part 3, the anti-Influenza A monoclonal-antibody solid phased membrane 4, and another filter as the water suction paper 5 have been pasted on adhesive resin (adhesive back sheet) such that the ends of the above adjacent members overlap in about 3 [mm], thereby producing the reagent device 10 for Influenza A virus detection.

<Production of First Sensitizer Pot>

At least one kind of surface active agent and buffer solution containing iron nitrate have been prepared to produce the first sensitizer.

After having dispensing 185 [μL] of the first sensitizer to a molded article of the first pot 133, the first pot 133 has been sealed by means of an aluminum sheet.
<Production of Second Sensitizer Pot>

Solution containing 10 weight % of silver nitrate has been prepared to produce the second sensitizer.

After having dispensed 95 [μL] of the second sensitizer to another molded article of the second pot 134, the second pot 134 has been sealed by means of another aluminum sheet.
<Production of Intermediate Plate>

The produced pots 133 and 134 have been installed in a plastic molded article for the intermediate plate.

A glass fiber filter has been cut into pieces of suitable sizes, and the pieces have been attached with a cleaning fluid-added pad 131 and the cleaning fluid-absorbing pad 132, respectively, thereby producing the intermediate plate 130.
<Production of Inspection Kit>

In Example 1, the reagent device 10 for detecting influenza has been installed onto the lower case 120 provided with the second slits according to the present method, the intermediate plate 130 has been held within the lower case 120, and the upper case 110 provided with the first slits according to the present method has been attached thereto, thereby producing the inspection kit 11.

In Comparative Example 1, the inspection kit has been produced as the same as the above except using the upper case with no slit and the lower case with no slit (neither shown).
<Measurement>

Eight negative samples containing no influenza virus antigen, and eight positive samples each containing Influenza A virus antigens have been extracted to 500 [μL] of extraction liquid by means of: the inspection kit in Example 1 according to the present method; and the inspection kit in Comparative Example 1.

The extraction liquid has been regarded as the sample, four drips of the appropriate amount and eight drips of the surplus amount thereof have been dripped onto the respective inspection kit, thereby performing the respective measurement.

Existence of Influenza A virus has been confirmed by means of the sample having checked in accordance with the PCR method.

The respective measurement has been performed by means of an exclusive measurement apparatus (not shown).

Immediately after having dripped the respective sample onto the respective inspection kit, the respective dripped inspection kit has been set up into the exclusive measurement apparatus.

In the exclusive measurement apparatus, after about 10 minutes of normal development as general immunochromatography, the respective measurement has been performed, and succeedingly after that, using a rod (not shown) of the exclusive measurement apparatus, the intermediate plate 130 of the respective inspection kits has been pushed against the reagent device 10 to keep depressing the first sensitizer pot 133, thereby making the first sensitizer (reducing agent) develop from the cleaning fluid-added pad 131 to the cleaning fluid-absorbing pad 132.

About 90 seconds after that, the second sensitizer pot 134 has been made develop to perform the sensitization reaction.

The exclusive measurement apparatus automatically has read line-like color development both at the control line part 4b and the detection line part 4a, and has performed positive/negative result according to the intensity of the respective color development.

Herein, if the intensity of the color development at the control line part 4b is less than the threshold, it is regarded that the reaction is not normally made resulting in an error, in other words, the determination is impossible.

The following table shows results thereof.

TABLE 1

| | dripped amount | | | | | | | | | | | | | | | |
|---|---|---|---|---|---|---|---|---|---|---|---|---|---|---|---|---|
| | 4 drips (appropriate amount about 140 µl) | | | | | | | | 8 drips (surplus amount about 280 µl) | | | | | | | |
| samples | 1 | 2 | 3 | 4 | 5 | 6 | 7 | 8 | 1 | 2 | 3 | 4 | 5 | 6 | 7 | 8 |
| Example 1 (8 positive samples) | + | + | + | + | + | + | + | + | + | + | + | + | + | + | + | + |
| Comp-Example 1 (8 positive samples) | + | + | + | + | + | + | + | + | + | E | + | E | E | + | E | - |
| Example 1 (8 negative samples) | - | - | - | - | - | - | - | - | - | - | - | - | - | - | - | - |
| Comp-Example 1 (8 negative samples) | - | - | - | - | - | - | - | - | + | - | E | - | - | - | E | + |

+: positive determination
-: negaitive determination
E: error

<Measurement Result>

In first cases of four drips of the appropriate amount, in both Example 1 and Comparative Example 1, negative result has been made with respect to all of the eight negative samples; and positive result has been made with respect to all of the eight positive samples.

Meanwhile, in second cases of eight drips of the surplus amount, in Comparative Example 1, labeled particles have not been able to fully flow, and the intensity of the color development at the control line part 4b has not been enough. Two cases of the negative samples and four cases of the positive samples have been judged as errors.

Furthermore, the false positive result has been made with respect to two cases among the eight negative samples, and the false negative result has been made with respect to one case among the eight positive samples.

Whereas, in Example 1, although in the second cases of the eight drips of the surplus amount, the true negative result has been made with respect to all of the eight negative samples, and the true positive result has been made with respect to all of the positive samples. In other words, neither an error nor false determination has been made.

Example 2

<Measurement of Adenovirus According to Immunochromatography Sandwich Method>

With a usual method, a colored particle-labeled antibody application part 3 has been produced and used by: having made anti-adenovirus (hexone protein) monoclonal antibodies bond with gold colloid to produce colored particle-labeled antibodies; having diluted the produced colored particle-labeled antibodies with the buffer solution to produce colored solution; and having applied the colored solution onto a glass fiber filter to be dried thereon.

Also the solid phased-antibody membrane 4, with a usual method, has been produced by having made anti-adenovirus monoclonal antibodies bond with the nitrocellulose membrane.

The reagent device 10 has been produced by having pasted: the filter of the sample-dripping part 2; the colored particle-labeled antibody application part 3; the antibody solid phased membrane 4; and the water suction paper 5 on an adhesive sheet 1 such that the ends of the above adjacent members overlap in about 3 [mm].

In Example 2, the inspection kit 11 has been produced by: having installed the prepared reagent device 10 onto the lower case 120 provided with the second slits; and having attached the upper case 110 provided with the first slits thereto.

In Comparative Example 2, the inspection kit has been produced as the same as the above except using the upper case with no slit and the lower case with no slit (neither shown).

In Example 2, without the sensitizing reaction, determination has been made by judging the presence of the line-like color development 10 minutes after having dripped a sample according to the general immunochromatography method.

The positive samples have been prepared by having diluted extraction liquid containing adenovirus antigens (concentration: $1*10^7$ TCID 50/mL) and at least one kind of surface active agents.

The negative samples have been prepared as the same as the above except containing no adenovirus antigen.

In both Example 2 and Comparative Example 2, four drips (about 140 [µL]) of the appropriate amount of the samples, and eight drips (about 280 [µL]) of the surplus amount of the samples have been dripped onto five tests, respectively, and 10 minutes after the reaction, determination has been made based on the line-like color development.

The following table shows results thereof.

TABLE 2

| samples | | 4 drips (appropriate amount 140 μL) | | | | | 8 drips (surplus amount 280 μL) | | | | |
|---|---|---|---|---|---|---|---|---|---|---|---|
| Example 2 | D line | + | + | + | + | + | + | + | + | + | + |
| (positive sample) | C line | + | + | + | + | + | + | + | + | + | + |
| Comp-Example 2 | D line | + | + | + | + | + | − | − | − | + | +W |
| (positive sample) | C line | + | + | + | + | + | +W | +W | + | + | + |
| Example 2 | D line | − | − | − | − | − | − | − | − | − | − |
| (negative sample) | C line | + | + | + | + | + | + | + | + | + | + |
| Comp-Example 2 | D line | − | − | − | − | − | − | − | − | − | − |
| (negative sample) | C line | + | + | + | + | + | + | + | + | +W | + |

+w: positive but too weak

In third cases of four drips of the appropriate amount, in both Example 2 and Comparative Example 2, positive result has been correctly made with respect to all of the positive samples, and the control lines have strongly colored.

Meanwhile, in fourth cases of eight drips of the surplus amount, in Example 2, positive result has been correctly made with respect to all of the positive samples. However, in Comparative Example 2, false negative result have been made in three examples among the five examples, and two examples of the positive sample and one example of the negative sample have been recognized that the control lines have colored not enough.

Having carefully observed the inside of the reagent devices 10 related to the false negative result, it has been revealed that the labeled particles have not been able to move enough to remain within the labeled-particle application part 3.

Embodiment 2

Figure 10:
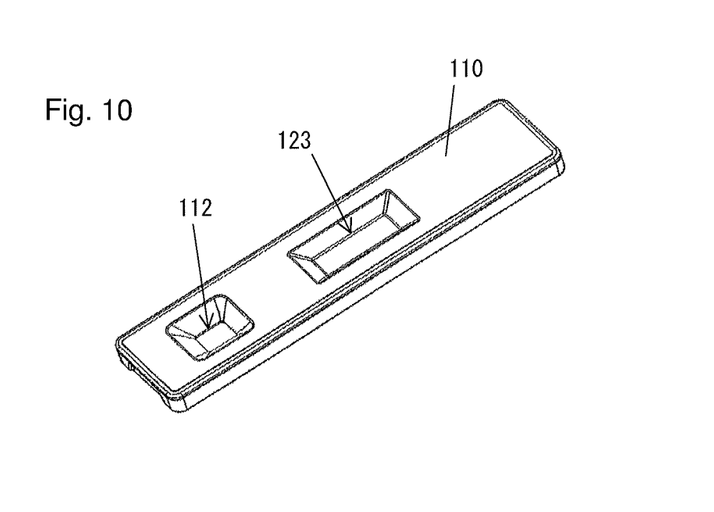
FIG. 10 is a perspective view of an upper case in Embodiment 2 according to the present invention.
Figures 11A, 11B:
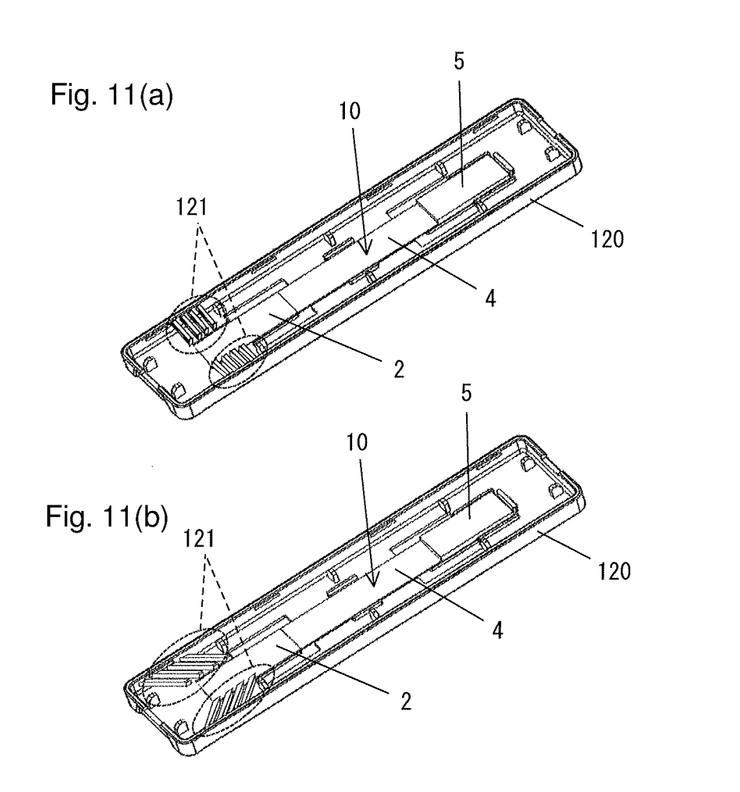
Figure 12A:
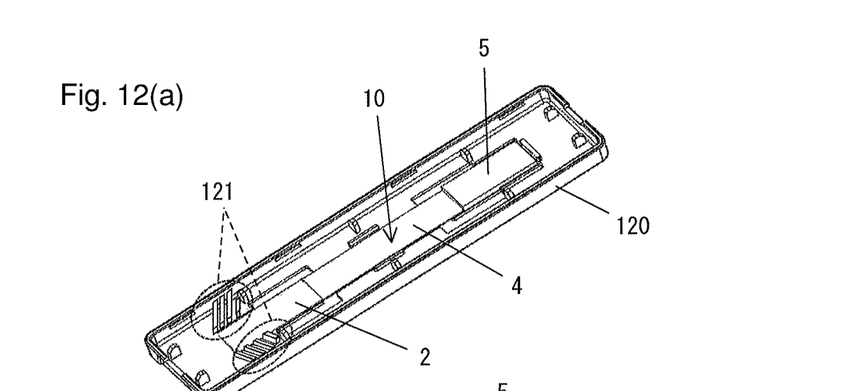
Figure 12B:
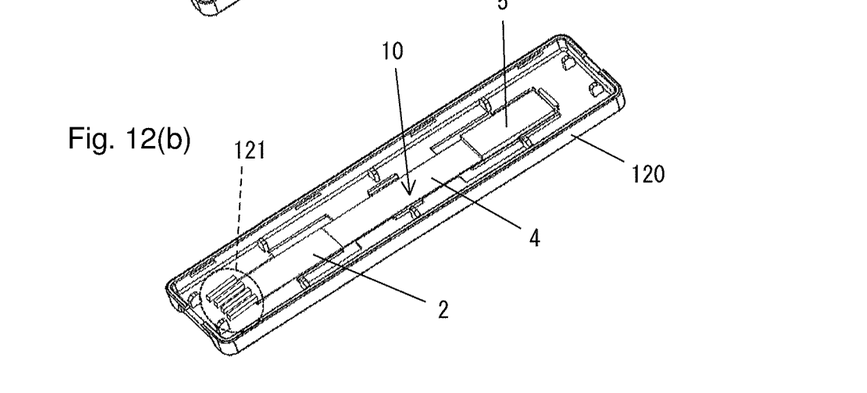

FIG. 10 is a perspective view of an upper case in Embodiment 2 according to the present invention, FIG. 11 (a) is a perspective view of a lower case and a reagent device in Embodiment 2 (Example 1) according to the present invention, FIG. 11 (b) is a perspective view of a lower case and a reagent device in Embodiment 2 (Example 2) according to the present invention, FIG. 12 (a) is a perspective view of a lower case and a reagent device in Embodiment 2 (Example 3) according to the present invention, and FIG. 12 (b) is a perspective view of a lower case and a reagent device in Embodiment 2 (Example 4) according to the present invention.

In Embodiment 1, the sensitization reaction has been used.

Whereas in Embodiment 2, the sensitizing reaction is not used, samples are developed according to the general immunochromatography method, and after a fixed time line-like color development is read.

Therefore, the intermediate plate in Embodiment 1 is omitted. The case is composed of: the upper case 110 shown in FIG. 10; and the lower case 120 shown in FIG. 11 (a) through FIG. 12 (b).

In FIG. 10, slits of the upper case 110 are not shown. The slits may be provided with the upper case 110, or may be omitted instead.

An automatic measuring apparatus may photograph, for example, a portion near the detection window 123 of the upper case 110 to perform measurement and determination in Embodiment 2.

Of course, a tester may drip a sample according to a manual method, and after a fixed time may confirm the existence of color development with his/her eyes.

As shown in FIG. 11 (a) as Example 1, it is the most preferable that the second direction in which the slits are formed intersects perpendicularly to the first direction in which the sample flows from the sample-dripping part 2.

However, as shown in FIG. 11 (b) as Example 2 and FIG. 12 (a) as Example 3, respectively, the second direction may intersect not perpendicularly to the first direction, and the second and first directions may be mutually oblique.

Furthermore, as shown in FIG. 12 (b) as Example 4, it is practically sufficient that the first direction and the second direction are opposite to each other (herein, the first direction and the second direction are parallel.).

As shown in the above, a portion where the liquid-absorbing part is arranged can be optionally selected as long as the sample-dripping part 2 is near thereof.

Taking the costs into consideration, it is preferable to integrally mold both the upper case 110 and the lower case 120 with the same plastic.

Furthermore, the upper case 110 and the lower case 120 may not be separated with each other but be partially belt-like connected to each other. If so, they can be folded up to be attached with each other.

Points other than the above are the same as those of Embodiment 1.

Having described preferred embodiments of the invention with reference to the accompanying drawings, it is to be understood that the invention is not limited to those precise embodiments, and that various changes and modifications may be effected therein by one skilled in the art without departing from the scope of the invention as defined in the appended claims.

What is claimed is:

1. An inspection kit, comprising:
   a reagent device having a sample-dripping part, the reagent device being capable of making a sample dripped on the sample-dripping part flow in a first direction from an upstream side toward a downstream side; and
   a case surrounding the reagent device,
   wherein: a liquid-absorbing part is provided with a portion near the sample-dripping part of the case, the liquid-absorbing part guiding, according to capillary action, a remainder of the sample in a second direction differing from the first direction in a same horizontal section; and
   the liquid-absorbing part includes a plurality of slits being alternately arranged.

2. The inspection kit as defined in claim 1, wherein the second direction intersects the first direction.

3. The inspection kit as defined in claim 2, wherein the second direction orthogonally intersects the first direction.

4. The inspection kit as defined in claim 1, wherein the first direction and the second direction are opposite to each other.

5. The inspection kit as defined in claim 1, wherein the case includes:
- an upper case surrounding an upper part of the reagent device; and
- a lower case surrounding a lower part of the reagent device.

6. The inspection kit as defined in claim 5, wherein:
the case further includes an intermediate plate located between the upper case and the lower case; and
the intermediate plate includes:
a first sensitizer pot storing first sensitizer containing a reducing agent therein; and
a second sensitizer pot storing second sensitizer containing silver ion liquid therein.

\* \* \* \* \*

UNITED STATES PATENT AND TRADEMARK OFFICE
CERTIFICATE OF CORRECTION

PATENT NO. : 10,359,421 B2  
APPLICATION NO. : 15/520297  
DATED : July 23, 2019  
INVENTOR(S) : Kaori Shimada Page 1 of 1

It is certified that error appears in the above-identified patent and that said Letters Patent is hereby corrected as shown below:

On the Title Page

In Item (71), Lines 1-3, "Applicants: FUJIFILM Corporation, Tokyo (JP); MIZUHO MEDI CO., LTD., Saga (JP)" should read --Applicants: FUJIFILM Corporation, Tokyo (JP)--

Signed and Sealed this  
Eighth Day of October, 2019

Andrei Iancu  
*Director of the United States Patent and Trademark Office*